United States Patent [19]

Mutsaers et al.

[11] Patent Number: 5,238,831
[45] Date of Patent: Aug. 24, 1993

[54] STABILIZATION OF CARBOXYL ESTERASE

[75] Inventors: Johanna H. G. M. Mutsaers, Utrecht; Cornelis J. van der Laken, Leiden; Cornelis P. Broekhuizen, Delft; Wilhemus J. Quax, Voorschoten, all of Netherlands

[73] Assignee: Gist-brocades, Netherlands

[21] Appl. No.: 884,465

[22] Filed: May 14, 1992

Related U.S. Application Data

[63] Continuation of Ser. No. 515,736, Apr. 26, 1990, abandoned, which is a continuation-in-part of Ser. No. 366,124, Jun. 14, 1989, abandoned.

[30] Foreign Application Priority Data

Apr. 28, 1989 [EP] European Pat. Off. ........... 89201107

[51] Int. Cl.$^5$ .......................... C12P 7/40; C12P 7/52; C12N 9/18; C12N 9/96
[52] U.S. Cl. .................................. 435/136; 435/141; 435/196; 435/197; 435/188
[58] Field of Search ............... 435/196, 197, 188, 141, 435/136; 530/402

[56] References Cited

U.S. PATENT DOCUMENTS 4,101,380 7/1978 Rubinstein et al. ................... 195/63
4,886,750 12/1989 Bertala et al. ......................... 435/136

OTHER PUBLICATIONS

Royer et al., "Cross-Linking of Reversibly Immobilized Enzymes", FEBS Letters, 80:1, Aug. 1977, pp. 89–94.
Lombardo, D., "Catalytic Properties of Modified Human Pancreotic Carboxylic Ester Hydrolase", Biochemica et Biophysica Acta, 700(1), 75–80, 1982.

Primary Examiner—Robert A. Wax
Assistant Examiner—Keith D. Hendricks
Attorney, Agent, or Firm—Morrison & Foerster

[57] ABSTRACT

Carboxyl esterase is inactivated by several chemical compounds such as naproxen or diclofop. By substituting or modifying certain basic residues of the carboxyl esterase, this enzyme shows improved stability properties during application. In this way it is possible to perform stereospecific hydrolysis reactions on industrial scale even at high substrate concentrations.

16 Claims, 4 Drawing Sheets

```
           10        20        30        40        50        60        70        80
ATGTCAAACCATTCATCTAGTATTCCCGAATTAAGTGACAACGGTATCCGCTATTATCAAACTTATAATGAAAGCCTTAG
 M  S  N  H  S  S  S  I  P  E  L  S  D  N  G  I  R  Y  Y  Q  T  Y  N  E  S  L  S
           90       100       110       120       130       140       150       160
TCTTTGGCCGGTCCGTTGCAAATCATTCTATATATCTACTCGTTTTGGTCAAACACATGTGATTGCAAGCGGCCCAGAGG
  L  W  P  V  R  C  K  S  F  Y  I  S  T  R  F  G  Q  T  H  V  I  A  S  G  P  E
          170       180       190       200       210       220       230       240
ATGCCCCGCCGCTTGTATTACTCCACGGAGCATTATTCAGCTCGACGATGTGGTATCCCAACATCGCCGATTGGAGCAGC
 D  A  P  P  L  V  L  L  H  G  A  L  F  S  S  T  M  W  Y  P  N  I  A  D  W  S  S
          250       260       270       280       290       300       310       320
AAATACAGAACTTATGCAGTTGATATCATAGGTGATAAAAACAAGAGTATTCCTGAGAATTTAAGCGGTACAAGAACGGA
 K  Y  R  T  Y  A  V  D  I  I  G  D  K  N  K  S  I  P  E  N  L  S  G  T  R  T  D
          330       340       350       360       370       380       390       400
TTACGCCAATTGGCTTCTTGATGTGTTTGACAATCTGGGGATCGAAAAGTCCCACATGATCGGACTTTCGCTTGGCGGTC
 Y  A  N  W  L  L  D  V  F  D  N  L  G  I  E  K  S  H  M  I  G  L  S  L  G  G
          410       420       430       440       450       460       470       480
TCCATACGATGAATTTCCTTTTACGTATGCCTGAGAGAGTAAAAAGCGCAGCTATACTGAGTCCAGCAGAAACGTTTTTG
 L  H  T  M  N  F  L  L  R  M  P  E  R  V  K  S  A  A  I  L  S  P  A  E  T  F  L
          490       500       510       520       530       540       550       560
CCATTTCATCACGATTTCTACAAATACGCTCTTGGCCTTACAGCGTCAAATGGGGTTGAAAAATTCTTAAATTGGATGAT
 P  F  H  H  D  F  Y  K  Y  A  L  G  L  T  A  S  N  G  V  E  K  F  L  N  W  M  M
          570       580       590       600       610       620       630       640
GACTGATCAGAATGTGCTGCACCCGATTTTTGTGAAGCAGTTTCAGGCAGGGGTAATGTGGCAGGATGGATCAAGAAATC
 T  D  Q  N  V  L  H  P  I  F  V  K  Q  F  Q  A  G  V  M  W  Q  D  G  S  R  N
          650       660       670       680       690       700       710       720
CAAATCCTAAAGCCGACGGATTTCCGTATGTTTTTACCGATGAGGAATTACGTTCAGCAAGAGTTCCTATCCTATTATTA
 P  N  P  K  A  D  G  F  P  Y  V  F  T  D  E  E  L  R  S  A  R  V  P  I  L  L  L
          730       740       750       760       770       780       790       800
CTTGGTGAACATGAAGTCATCTATGATCCCCACTCAGCCCTGCACCGAGCCTCTTCATTCGTTCCTGATATTGAGGCGGA
 L  G  E  H  E  V  I  Y  D  P  H  S  A  L  H  R  A  S  S  F  V  P  D  I  E  A  E
          810       820       830       840       850       860       870       880
AGTCATTAAAAAATGCCGGACATGTTTTATCGATGGAACAACCCGCTTACGTAAATGAACGTGTAATGCGTTTTTTCAATG
 V  I  K  N  A  G  H  V  L  S  M  E  Q  P  A  Y  V  N  E  R  V  M  R  F  F  N
          890       900
CAGAAACAGGCATTTCACGGTAA
 A  E  T  G  I  S  R  *
```

FIG.1

STABILIZATION OF CARBOXYL ESTERASE

This application is a continuation of application Ser. No. 07/515,736, filed Apr. 26, 1990, which application is a continuation-in-part of Ser. No. 07/366,124, filed Jun. 14, 1989, both now abandoned.

TECHNICAL FIELD

The present invention relates to the stabilization of carboxyl esterase.

BACKGROUND AND RELEVANT LITERATURE

U.S. Pat. No. 4,886,750 discloses the use of esterases in the stereoselective hydrolysis of esters of 2-arylpropionic acids. In this document the enzyme responsible for the hydrolysis of (S)-naproxen esters is characterized. The corresponding esterase gene was obtained from the *Bacillus subtilis* Thai 1-8 strain (CBS 679.85). This gene encoding the enzyme responsible for the stereoselective conversion of (R,S)-naproxen ester was cloned in *E. coli* and *Bacillus subtilis*. It was found that the esterase activity was improved by introducing multiple gene copies in several *Bacillus subtilis* (a.o. CBS 673.86). The suitability of the microorganism and the enzyme derived therefrom for use in a process to hydrolyse S-naproxen ester was therefore also improved.

In said U.S. patent only low substrate concentrations (naproxen or ibuprofen) are used. In contrast, commercial applications require high product concentrations in order to obtain economically attractive results. However, during tests at high substrate concentrations (commercial conditions) irreversible inactivation of the enzyme has been noticed. For example, carboxyl esterase obtained from Bacillus Thai I-8 was almost completely inactivated within one hour when 30 g/l naproxen ester was added (pH=9, T=40° C. and Tween 80 TM medium). The esterase as such is stable at pH=9 and T=40° C. (with and without Tween 80 TM) for several hours. During the stereoselective hydrolysis of (R,S)-naproxen ester, the enzyme was inactivated by the naproxen formed during the hydrolysis. High yields of naproxen could not therefore be obtained.

The enzyme carboxyl esterase may be used in several other stereospecific esterase hydrolysis reactions. However, it is found that the product (the acid) of these reactions often inactivates the enzyme when the reaction takes place at commercially interesting starting concentrations of the ester.

The carboxyl esterase can be used in the stereospecific hydrolysis of diclofop esters, resulting in the corresponding enantiomeric pure (S)-acid, which process is described in EP-A-0299559. The diclofop formed will inactivate the enzyme under commercially attractive conversion conditions.

Other compounds that inactivate the enzyme are, for example, 2-naphthoxy acetic acid, ibuprofen, 2-naphthol and phenol.

In the literature enzymes are known to become inactivated because of their low thermal stability. At elevated temperatures unfolding of the enzyme may take place. Heat treatment causes especially the hydrogen bonds to break (see e.g. R. D. Schmid, Advances in Biochemical Engineering 12, Ghose, Fiechler & Blakebrough (Eds), Springer, Berlin (1979) pp. 41-115). Thermo unfolding of enzymes can, however, be diminished by immobilization or cross-linking of the enzyme. For example, cross-linking with glutaraldehyde improved the thermostability of Papain (Royer et al., FEMS Lett. 80 (1977) 1) and Subtilopeptidase (Boudrant et al., Biotechnol. Bioeng. 18 (1976) 1719).

Even the mechanism of thermostabilisation is not well understood. E. T. Reese and M. Manders (Biotechnol. Bioeng. 22 (2) 1980 pp. 326–336 showed that crosslinking (glutaraldehyde treatment) did not result in an increase of thermostability and activity of cellulase. Similar results were found by N. W. Ugarova (Biokhimiya 42 (7), 1977 pp. 1212-1220) who reported that modification of peroxidase with glutaraldehyde gave a 2.5-fold decrease in thermostability.

The prior art presents only very specific solutions for specific problems (immobilization and cross-linking techniques) which are not generally applicable. Moreover it has been noticed that the carboxyl esterase is not thermally inactivated at normal reaction conditions (up to 45° C.) but is only inactivated by certain compounds at reaction conditions. The prior art is silent on such kind of inactivations.

When the amino acid residue which is the cause of inactivation of the protein is known, an alternative approach to chemical modification is available. In that case one can replace the residue for another one by site-directed mutagenesis, as described for instance by Ausubel et al. (Current Protocols in Molecular Biology, John Wiley & Son Inc., 1987, New York). In this way e.g. the oxidation resistance of *B.alcaloohilus* serine protease was improved by replacing a methionine residue by a serine residue (European patent application no. 0328229).

The known stabilization techniques cannot be applied as such to the present enzyme because the nature of the inactivation is different when inactivation by chemical compounds plays a role.

SUMMARY OF THE INVENTION

The present invention relates to a modified carboxyl esterase which shows enhanced stability in the presence of compounds such as naproxen, and may be employed in the stereospecific hydrolysis of such compounds. Accordingly, the present invention provides a process for stereospecifically hydrolysing an optically active substrate which comprises hydrolysing the substrate in the presence of a carboxyl esterase which shows enhanced stability when contacted with 15 mg/ml of (S)-naproxen at 40° C. for 1.5 hours, compared to the wild type. This modified carboxyl esterase can be obtained by substituting or modifying at least one basic amino acid residue of the wild-type carboxyl esterase.

BRIEF DESCRIPTION OF THE FIGURES

FIG. 1 shows the nucleotide sequence of the coding region of the gene for carboxyl esterase from *Bacillus subtilis* Thai I-8 (CBS 679.85).

: unmodified enzyme
+: glutaric anhydride modified
*: succinic anhydride modified
☐: glyoxal modified
×: glutaric aldehyde modified
: formaldehyde modified.

Figure 5:
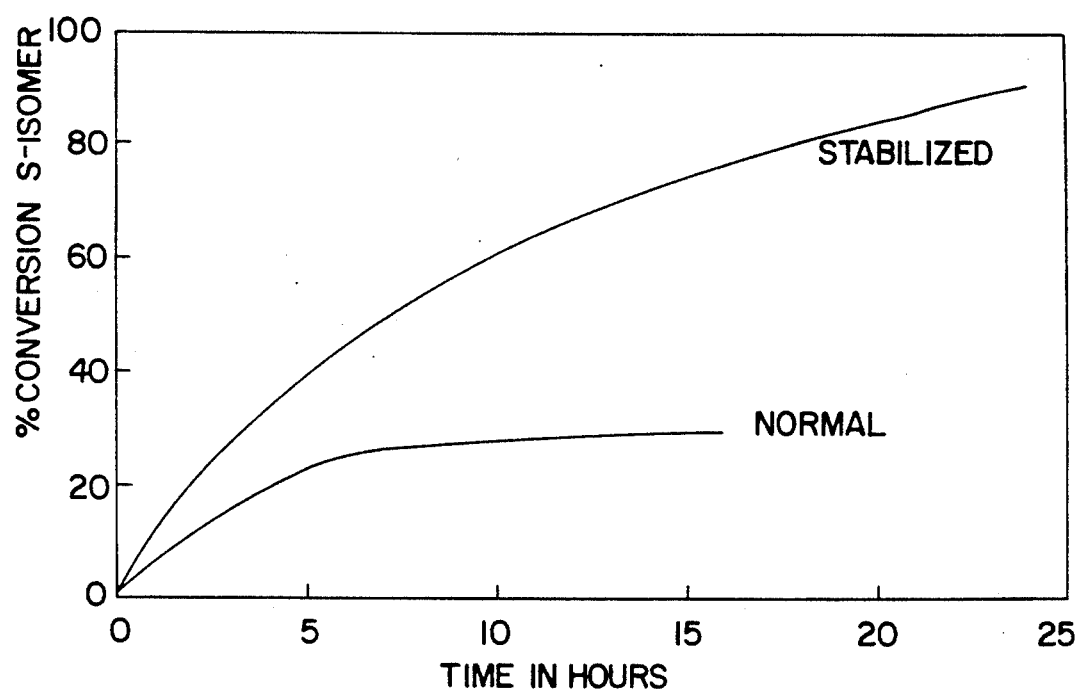

FIG. 5 shows the conversion of (R,S)-diclofop ethyl ester using carboxyl esterase and modified carboxyl esterase, respectively.

DESCRIPTION OF THE SPECIFIC EMBODIMENTS

It is to be understood that the term 'carboxyl esterase' as used throughout the present application denotes an esterase obtainable from a Bacillus strain and capable of stereospecifically hydrolysing S-naproxen.

Carboxyl esterase is stable at temperatures up to 45° C. In the presence of compounds like naproxen the enzyme is quickly inactivated. The enzyme substantially loses activity within 1.5 hours in the presence of 15 mg/ml (S)-naproxen at 40° C. The inactivation of the enzyme is accompanied by aggregation of the enzyme. This inactivation, or destabilisation is not due to thermo-inactivation but is found to be related to the chemical effect of compounds like naproxen on the enzyme. The present invention is based on the discovery that positively charged amino acid residues in the carboxyl esterase are involved in the destabilization. Possibly the naproxen acid reacts with the free amino groups at the surface of the enzyme, thereby allowing the hydrophobic bulk of the naproxen acid to interfere with the folding of the enzyme. This unfolding is noticed as increased susceptibility of the enzyme to proteolytic breakdown in the presence of naproxen. By substituting (protein engineering) or by chemically modifying these basic residues, the positive charge of these amino acids can be removed or reversed. This would prevent the binding of the naproxen acid to the enzyme. In this respect it is to be noticed that only small and not too hydrophilic chemical groups can be used to modify the enzyme. Benzaldehyde, for instance, does not have a positive effect on enzyme stability. Also, changing the positive charged residues to other residues with positive charge but less susceptible to chemical modification, such as lysine to arginine substitutions (see e.g. R. D. Schmid, Advances in Biochemical Engineering 12, Ghose, Fiechler & Blakebrough (Eds.), Springer, Berlin (1979), 41-115), might give rise to stabilization of the enzyme.

Accordingly, in a further aspect, the present invention provides a modified carboxyl esterase which has been produced by treating wild-type carboxyl esterase with a compound comprising at least one group which can react with a positively charged basic amino acid residue in the carboxyl esterase. This results in higher product concentrations and higher yields. Aldehydes (mono- or dialdehydes) such as formaldehyde, glutaraldehyde or glyoxal, and anhydrides such as glutaric acid anhydride or succinic anhydride, are examples of compounds which may be used to treat the carboxyl esterase.

Generally 0.05–10 v/v % (calculated on the reaction mixture) of the compound (stabilizing agent) is added to the reaction mixture containing the wild-type carboxyl esterase. Typically 0.1–5 v/v % of this agent is added. The pH is maintained during the stabilization of the enzyme at at least pH=7, typically at a pH from 7 to 10.

It is found that substantially all the carboxyl esterase is stabilized after addition of the compound such as aldehyde or anhydride. The fact that stabilization can occur using formaldehyde, a mono aldehyde, or an anhydride, indicates that the enzyme is being chemically modified by the formaldehyde or anhydride rather than intra molecular cross-linked.

According to a still further aspect of the present invention new enzymes are provided, in particular modified carboxyl esterases, which can be obtained by expression of genes encoding said enzyme, which differs from said wild-type esterase in at least one basic amino acid residue present in the corresponding wild-type enzyme and which exhibit improved properties during application. It has surprisingly been found that certain lysine, argine and histidine residues are involved in the inactivation of the carboxyl esterase.

The present invention thus provides a stabilized or modified enzyme, particularly a stabilised or modified carboxyl esterase, which has been produced by replacing at least one basic amino acid residue in the corresponding wild-type enzyme, and expressing the mutant gene or which basic amino acids are modified by the action of certain chemical compounds.

After determining the DNA sequence of carboxyl esterase (see Example 1), lysine, arginine and histidine residues of the esterase can be replaced by mutating the esterase gene with the technique of site directed mutagenesis (Ausubel et al., 1987, Current Protocols in Molecular Biology, John Wiley & Son Inc., New York). In this way the positively charged basic lysine and/or arginine residues can, for instance, be substituted by neutral (non charged) or negatively charged residues (e.g. glutamine, serine or glutamic acid). In the same way other residues (e.g. histidine), which are involved in the destabilisation of carboxyl esterase, can be substituted by other residues.

The modified enzyme shows improved properties during industrial application, for example, in the hydrolysis of naproxen ester. By improved properties as used herein we mean a high conversion performance arising from improved stability, and especially improved stability against certain chemical compounds, relative to the corresponding wild-type enzyme.

"Carboxyl esterase" as used herein means an esterase obtainable from a Bacillus strain, which is capable of stereospecifically hydrolysing S-naproxen ester. Preferably, the enzyme is substantially identical, or identical, to the esterase obtainable from a *Bacillus subtilis* strain, more preferably from the *Bacillus subtilis* Thai 1-8 strain (CBS 679.85). By an enzyme which is substantially identical to the esterase obtainable from the *Bacillus subtilis* Thai I-8 strain is meant that the DNA sequence encoding an esterase has at least 70% homology in the nucleotide sequence with the DNA sequence encoding for the esterase from *Bacillus subtilis* Thai I-8 strain.

The following equation, which has been derived from analysing the influence of different factors on hybrid stability:

$Tm = 81 + 16.6 \; (\log 10 \; Ci) + 0.4 \; (\% \; G+C) - 600/n - 1.5 \; (\% \; \text{mismatch})$ (Current protocols in molecular biology 1987–1988, edited by Ausubel et al.).

n = length of the shortest chain of the probe
Ci = ionic strength (M)
G+C = base composition
Tm = hybridization temperature was used to determine the homology which could be detected in our experiments. Assuming a probe length of 300 bases, we were able to detect a homologous gene which shows at least 67% homology within a fragment of 300 bases or more. In the determination of homology percentage we assumed that the GC contents of Bacillus is 50% (Normore, 1973, in Laskin and Lechevalier (ed), Handbook of Microbiology vol. II, CRC Press, Inc. Boca Raton. Fla.). This means that a modified carboxyl esterase with at least 70% homology with *Bacillus subtilis* Thai I-8 carboxyl esterase is comprised in the invention.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity and understanding, it will be readily apparent to those of ordinary skill in the art in light of the teachings of this invention that certain changes and modifications may be made thereto without departing from the spirit and scope of the appended claims.

The following examples further illustrate the invention.

EXAMPLE 1

Determination of the Amino Acid Sequence of Carboxyl Esterase of *Bacillus Subtilis* 1-85/pNAPT-7 (CBS 673.86)

The amino acid sequence of carboxyl esterase originating from *Bacillus subtilis* 1-85/pNAPT-7 (CBS 673.86), described in U.S. Pat. No. 4,886,750 was determined as follows. The nucleotide sequence of the 2.2 HindIII-HindIII insert fragment of pNAPT-7 was determined by the dideoxy chain termination method as described by Sanger et al. (Proc. Natl. Acad. Sci. USA 75 (1977), 5463). Within the sequence only one large open reading frame capable of encoding a 30 kD protein could be detected. From the nucleotide sequence of this open reading frame the amino acid sequence of this carboxyl esterase has been derived. FIG. 1 shows the DNA sequence and the derived amino acid sequence for this carboxyl esterase. The one letter code for amino acids is explained in the following table:

A = Alanine
L = Leucine
R = Arginine
K = Lysine
N = Asparagine
M = Methionine
D = Aspartic acid
F = Phenylalanine
C = Cysteine
P = Proline
Q = Glutamine
S = Serine
E = Glutamic acid
T = Threonine
G = Glycine
W = Tryptophan
H = Histidine
Y = Tyrosine
I = Isoleucine
V = Valine

EXAMPLE 2

Mutation of lysine residues in carboxyl esterase

The DNA fragment encoding carboxyl esterase in *Bacillus subtilis* Thai I-8 (CBS 679.85) (BclI-HindIII fragment of 2.0 kb originating from pNAPT-2, see EP-A-233656) was cloned into vector pTZ18R. Single stranded DNA was prepared according to the instructions of supplier (Pharmacia). This single stranded DNA was subjected to oligonucleotide directed mutagenesis as described (Ausubel et al., ibid.). Eleven different mutagenesis reactions were performed in order to substitute the eleven lysine residues of carboxyl esterase (see FIG. 1) one at a time by a glutamine residue. In addition a twelveth reaction was carried out in which a mixture of eleven different oligonucleotides, each encoding a different lysine → glutamine mutation, was included into the mutagenesis protocol. The resulting mutant esterase from reaction 1-11 was produced in *E. coli* DHI (ATCC 33849) as described in EP-A-233656 (with the deviation that vector pTZ18R instead of pUN121 was used) and tested for stability in the presence of (S)-naproxen (as described in Example 3). The mixture of mutants from reaction 12 was distributed into microtiter plates and tested for stability in the presence of naproxen using a color assay based on β-naphthol and fast-blue to determine residual activity of the mutant esterases. An automatic pipetting robot was used to screen 20.000 candidate mutants. More stable mutant enzymes originating from the twelve different mutagenesis reaction were selected and used for further characterization.

EXAMPLE 3

Stability of Mutant Carboxyl Esterases

Mutant carboxyl esterases constructed as described in Example 2 were tested for stability as follows: a solution of 9 ml containing 0.10 g (S)-naproxen was incubated at 40° C. for 15 minutes prior to the addition of 1 ml containing 24 U carboxyl esterase. The composition of the final mixture was 10 g/l naproxen, 1 mM MOPS, 20 mM glycine, 2.4 U/ml carboxyl esterase, pH 8.75. Immediately after addition of the enzyme solution and mixing, the first 50 µl sample was drawn (0 minute sample). At 0, 15, 30, 45, 60, 90, 120, 180 and 240 minutes incubation 50 µl samples were drawn and immediately diluted to 5 ml in 100 mM MOPS buffer pH 8.75 containing 0.2% BSA. Carboxyl esterase activity was assayed in these samples as described hereinbelow according to 'Analytical Methods'.

Several mutant enzymes with increased stability in the presence of naproxen were obtained, for instance mutants in which Lysine 34, Lysine 81 or Lysine 217 were replaced by Glutamine.

The majority of the constructed mutants showed decreased stability or decreased activity, as expected. However, the observation that out of eleven possible lysines, mutation of each of three positions can give rise to increased stability while retaining the activity of the enzyme, indicates the possibilities of site-directed mutagenesis. Furthermore, in this Example only mutations to glutamine were constructed. Replacement of lysines by other residues could also give good or even better results. In this respect, substitution of lysines by arginines would be preferred for the following reasons:

1. Arginine has the same positive charge as lysine;

2. The arginine epsilon amino group is less susceptible to modification by alkyl or carboxyl groups than that of lysine.

Also construction of better mutants by combination, based on the ones now available is feasible.

The inactivation profiles, as determined by assaying enzyme activity after increasing periods of incubation of the enzyme with 10 g/l naproxen as described above, is shown for three Lysine → Glutamine mutants and the wild-type enzyme in Table 1.

TABLE 1

| Time (min.) | Rest Activity (%) | | | |
|---|---|---|---|---|
| | Wild type | Lys 34 Glu | Lys 81 Glu | Lys 217 Glu |
| 0 | 100 | 100 | 100 | 100 |
| 15 | 79 | 93 | 67 | 87 |
| 30 | 56 | 81 | 63 | 71 |
| 45 | 43 | 81 | 54 | 60 |
| 60 | 34 | 75 | 49 | 53 |
| 90 | 24 | 68 | 42 | 38 |
| 120 | 14 | 61 | 25 | 26 |
| 180 | 6 | 49 | 13 | 15 |
| 240 | 4 | 38 | 8 | 8 |

Figure 2:
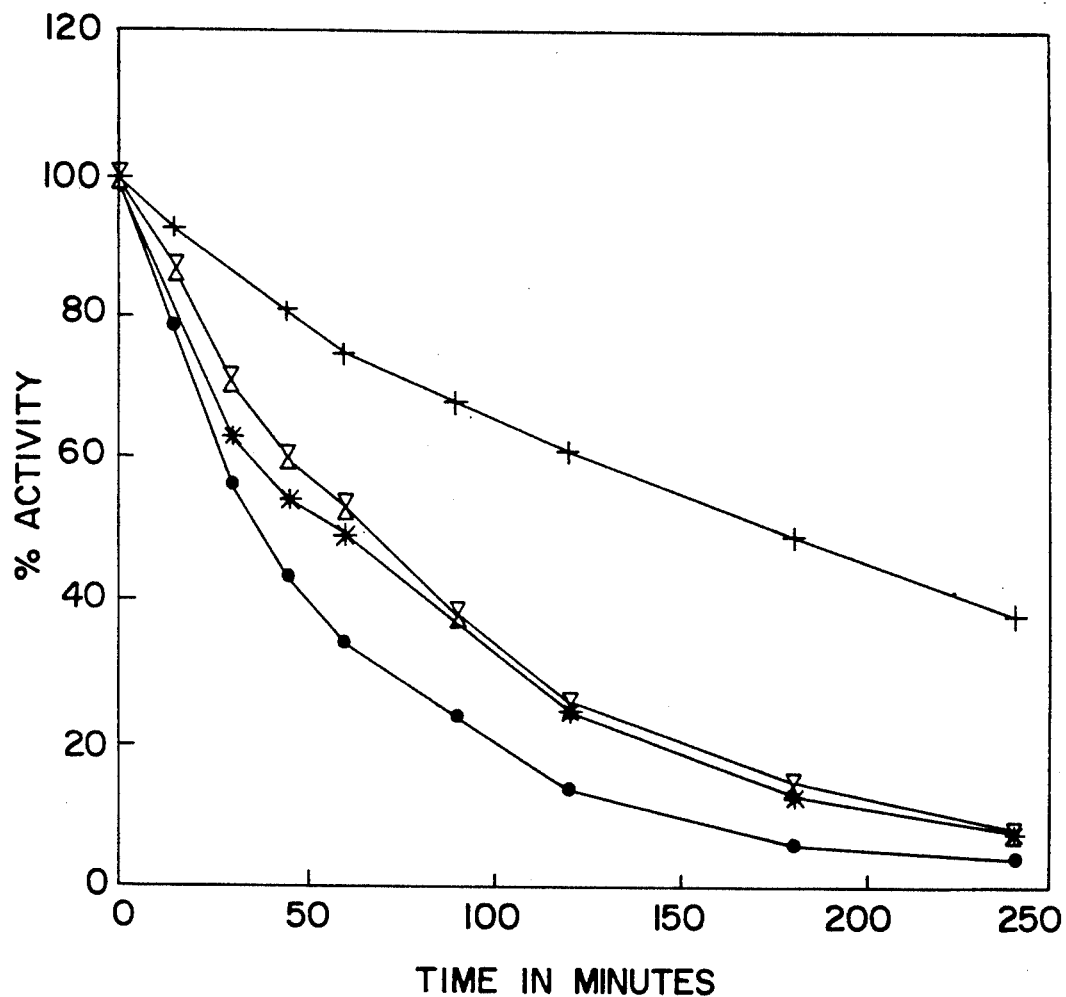
FIG. 2 shows the activity of the wild-type carboxyl esterase and several mutant carboxyl esterases;
: wild-type carboxyl esterase
+: Lys 34 Glu mutant
*: Lys 81 Glu mutant
: Lys 217 Glu mutant

These results are also depicted in FIG. 2.

ANALYTICAL METHODS

Carboxyl esterase is assayed in 0.1 M MOPS (3-[N-morpholino]propanesulfonic acid) pH 7.5 at 25° C. in the presence of 0.3 mg (S)-naproxen methyl ester per ml, 2% Tween 80 TM, 1 mg/ml BSA (Bovine Serum Albumin). The HPLC system used is a reversed phase column (Novapak CN Radial Pak cartridge from Waters) eluted with acetonitrile: 0.03M phosphate (34:66) pH 3.2 at a flow of 1.5 ml/min. Retention times found were 6.9 min for the methyl ester and 4.6 min for naproxen. 1 Unit (U) is defined as the amount of enzyme that hydrolyses $1 \times 10^{-6}$ mol (S)-naproxen methyl ester per minute under the conditions as specified below.

EXAMPLE 4

Carboxyl esterase preparation from *Bacillus subtilis* 1-85/pNAPT-7 and Bacillus licheniformis T9

*Bacillus subtilis* 1-85/pNAPT-7 (CBS 673.86) was grown as described in the European patent application no. EP-A-233656. The enzyme was isolated as described in Example 14 of that application. The ultrafiltration concentrate was lyophilized. The activity of the dried material was approximately 2400 U/g.

In another experiment pNAPT-7 was transformed into *Bacillus licheniformis* T9 using a protocol as described in EP-A-253455. This strain, which is protease negative, α-amylase negative and sporulation negative, is advantageous for fermentation and recovery of carboxyl esterase. The enzyme was obtained analogously as the esterase from *Bacillus subtilis* 1-85/pNAPT-7 and showed a similar activity. The activities are determined according to the "Analytical Methods" of Example 3.

EXAMPLE 5

Modification of Carboxyl Esterase by Formaldehyde

Carboxyl esterase (originating from *Bacillus subtilis* 1-85/pNAPT-7 (CBS 673.86)) solutions were prepared containing 40 mg/ml lyophilized enzyme, 250 mM MOPS (3-[N-morpholino]propanesulfonic acid) pH 7.5 and increasing formaldehyde concentrations (0.01–10%). The concentrations of the modifying agent are given as v/v % of the reaction mixture. The solutions were left to stand at 20° C. for one hour. Subsequently, part of the sample was used for direct enzyme activity determination and part of the sample was first incubated with 15 mg/ml (S)-naproxen at 40° C. for 1.5 hours before enzyme activity determination. The results are given in Table 2.

By rest activity is meant the activity left after a certain chemical treatment, relative to the activity without chemical treatment. The activities are determined according to the "Analytical Methods" of Example 3.

TABLE 2

| Formaldehyde % | Rest activity after formaldehyde treatment (in %) | Rest activity after formaldehyde treatment and incubation with naproxen (in %) |
|---|---|---|
| 0 | 100 | 2 |
| 0.01 | 105 | 7 |
| 0.025 | 99 | 7 |
| 0.05 | 100 | 8 |
| 0.1 | 95 | 20 |
| 0.25 | 93 | 45 |
| 0.5 | 87 | 60 |
| 1.0 | 64 | 61 |
| 2.5 | 47 | 45 |
| 5.0 | 36 | 41 |
| 10.0 | 11 | 16 |

Figure 3:
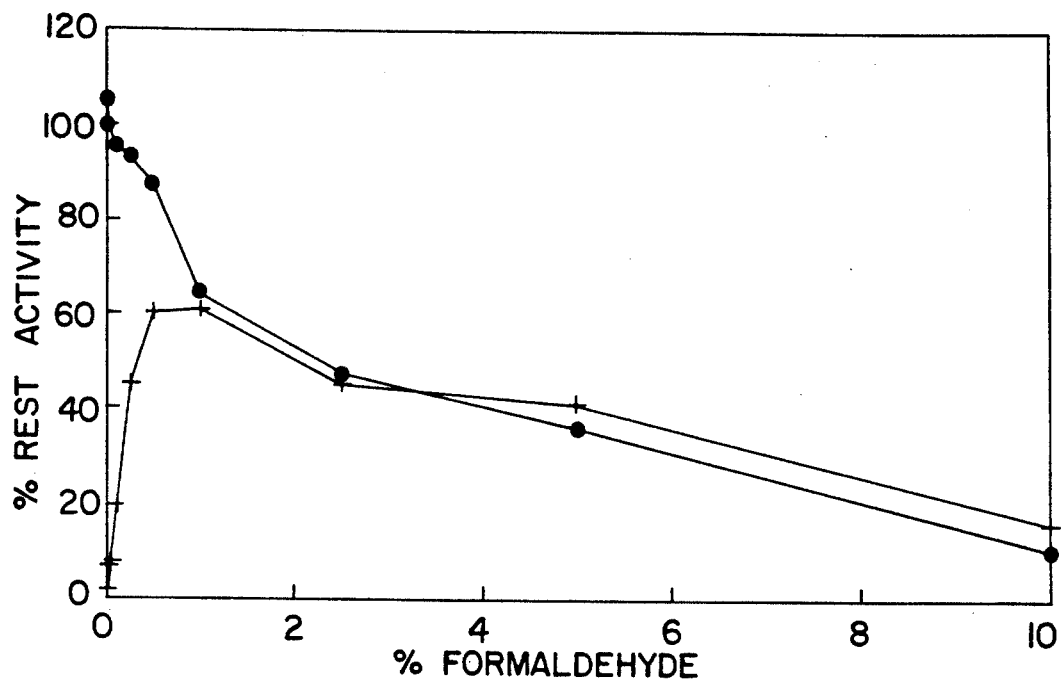
FIG. 3 shows the influence of formaldehyde treatment on the activity of the carboxyl esterase;
: after formaldehyde treatment
+: after formaldehyde and naproxen treatment.

The results are also depicted in FIG. 3. It is shown that the untreated enzyme is completely inactivated on incubation with naproxen for 1.5 hours at 40° C. Formaldehyde treatment of the esterase gives rise to a partial loss of activity. However, the modified enzyme, treated with formaldehyde concentrations of 1% or higher, is completely stable on incubation with naproxen (15 mg/ml) for 1.5 hours at 40° C.

EXAMPLE 6

Modification of Carboxyl Esterase with Formaldehyde

Carboxyl esterase (originating from *Bacillus subtilis* 1-85/pNAPT-7 (CBS 673.86)) solution containing 10 mg/ml lyophilized enzyme, 250 mM MOPS, pH 7.5 and 2% formaldehyde was stirred at 20° C. for one hour. The sample was dialyzed against 100 mM MOPS pH 7.5. The esterase activity was determined according to the "Analytical Methods" of Example 3; the rest activity was 60%.

EXAMPLE 7

Modification of Carboxyl Esterase with Glutaraldehyde

Carboxyl esterase (originating from *Bacillus subtilis* 1-85/pNAPT-7 (CBS 673.86)) solution containing 10 mg/ml lyophilized enzyme, 250 mM MOPS, pH 7.5 and 2% glutaraldehyde was stirred at 20° C. for one hour. The sample was dialyzed against 100 mM MOPS pH 7.5. The esterase activity was determined according to the "Analytical Methods" of Example 3; the rest activity was 68%.

EXAMPLE 8

Modification of Carboxyl Esterase with Glyoxal

Carboxyl esterase (originating from *Bacillus subtilis* 1-85/pNAPT-7 (CBS 673.86)) solution containing 20 mg/ml lyophilized enzyme, 250 mM carbonate, pH 9.2 and 0.8% glyoxal was stirred at 20° C. for one hour. The sample was dialyzed against 250 mM carbonate pH 9.2. The esterase activity of the material was determined according to the "Analytical Methods" of Example 3; the rest activity was 45%.

EXAMPLE 9

Modification of Carboxyl Esterase with Succinic Anhydride

Carboxyl esterase (originating from *Bacillus subtilis* 1-85/pNAPT-7 (CBS 673.86)) solution containing 10 mg/ml lyophilized enzyme, 0.5 M MOPS, pH 8.0 and 0.3% succinic anhydride was stirred at 20° C. for one hour. The esterase activity was determined according to the "Analytical Methods" of Example 3; the rest activity was 62%.

EXAMPLE 10

Modification of Carboxyl Esterase with Glutaric Anhydride

Carboxyl esterase (originating from *Bacillus subtilis* 1-85/pNAPT-7 (CBS 673.86)) solution containing 10 mg/ml lyophilized enzyme, 0.5M MOPS, pH 8.0 and 0.3% glutaric anhydride was stirred at 20° C. for one hour. The esterase activity was determined according to the "Analytical Methods" of Example 3; the rest activity was 72%.

EXAMPLE 11

Figure 4:
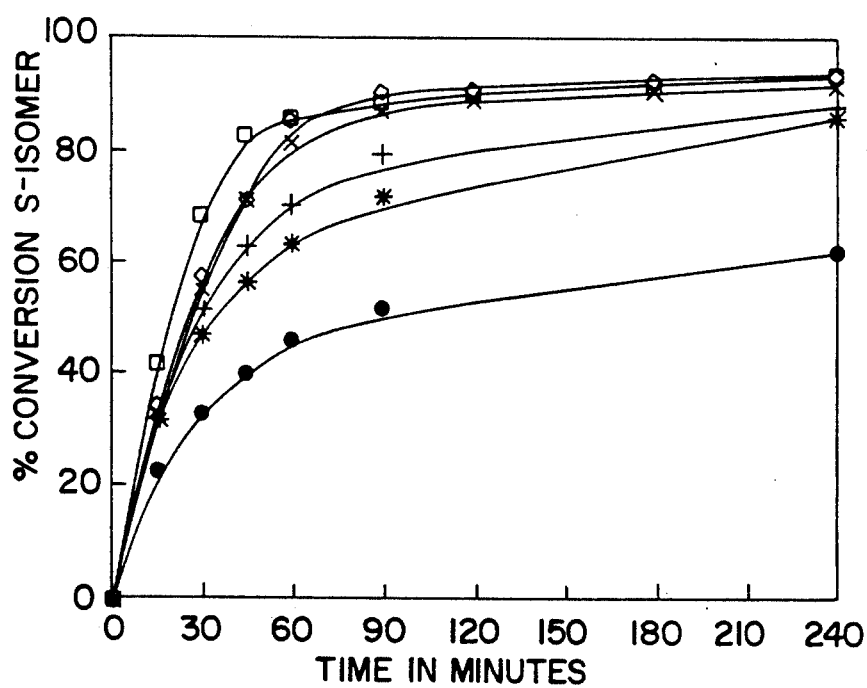
FIG. 4 shows the conversion of naproxen ester using carboxyl esterase and the modified carboxyl esterase.

(R,S)-naproxen methyl ester conversion with modified carboxyl esterase 300 mg of (R,S)-naproxen methyl ester was added to 10 ml 2% Tween 80 TM. The pH was adjusted to 9.0. Subsequently 5.5 U of modified enzyme, prepared as described in Examples 6-10, were added. The pH was kept at 9.0 by titration with 2.5M ammonium hydroxide. The reaction was carried out at 40° C. The extent of conversion was followed in the time by HPLC. A conversion with unmodified enzyme was used as a reference. The results, depicted in FIG. 4, show that the modified enzymes reach a much higher conversion than the untreated enzyme.

EXAMPLE 12

(R,S)-diclofop ethyl ester conversion with glutaraldehyde modified carboxyl esterase.

750 mg (R,S)-diclofop ethyl ester was added to 25 ml 1% Tween 80 TM. The pH was adjusted to 9.0. Subsequently 10 U of modified enzyme were added. The modified enzyme was obtained as described in Example 7 except that only 0.15% of glutaraldehyde was added. The pH was kept at 9.0 by titration with 0.1M NaOH. The temperature was 20° C. The extent of conversion was followed in the time by HPLC. A conversion with unmodified enzyme was used as a reference. The results, depicted in FIG. 5, show that the modified enzyme reaches a much higher conversion than the untreated enzyme.

We claim:

1. Modified carboxyl esterase, obtained by chemically modifying a wild-type carboxyl esterase with an effective amount of a compound selected from the group consisting of an aldehyde, an anhydride, and mixtures thereof sufficient to modify said carboxyl esterase, wherein said modified carboxyl esterase shows enhanced stereospecific hydrolysis of (R,S)-naproxen esters and enhanced stability for naproxen when contacted with 15 mg/ml of (S)-naproxen at about pH-9 and at 40° C. for 1.5 hours as compared to the corresponding wild-type carboxyl esterase.

2. Modified carboxyl esterase according to claim 1 whereby the the compound is an aldehyde or anhydride, selected from the group consisting of formaldehyde, glutaraldehyde, glyoxal, glutaric anhydride and succinic anhydride.

3. Modified carboxyl esterase according to claim 1 wherein the wild-type carboxyl esterase is substantially identical to the carboxyl esterase obtained from a *Bacillus subtilis* strain.

4. Modified carboxyl esterase according to claim 3 wherein the wild-type carboxyl esterase is substantially identical to the carboxyl esterase obtained from *Bacillus subtilis* Thai I-8 (CBS 679.85).

5. The modified carboxyl esterase of claim 1 wherein the treatment is with formaldehyde.

6. A method to stabilize wild-type carboxyl esterase during enhanced stereospecific hydrolysis of (R,S)-naproxen esters, which method comprises treating said wild-type esterase with a reagent capable of neutralizing the positively charged basic amino acid residues of said esterase thereby enhancing stability of said esterase when contacted with 15 mg/ml of (S)-naproxen, at about pH-9 and at 40 ° C. for 1.5 hours as compared to untreated wild-type carboxyl esterase, said reagent selected from the group consisting of an aldehyde, an anhydride and mixtures thereof sufficient to modify said carboxyl esterase.

7. The method of claim 6 wherein said aldehyde is selected from the group consisting of formaldehyde, gluteraldehyde and glyoxal.

8. The method of claim 6 wherein said anhydride is glutaric anhydride or succinic anhydride.

9. A modified carboxyl esterase prepared by the method according to claim 6.

10. The method of claim 7 wherein the aldehyde is formaldehyde.

11. A method to conduct stereospecific hydrolysis of an ester, which method comprises contacting said ester with an amount of the modified carboxyl esterase of claim 1 effective to result in said stereospecific hydrolysis.

12. A method according to claim 11 in which an (R,S)-2-substituted propionic acid ester is stereospecifically hydrolysed to give the corresponding enantiomeric (S)-acid.

13. A method to conduct stereospecific hydrolysis of an ester, which method comprises contacting said ester with an amount of the modified carboxyl esterase of claim 9, effective to result in said stereospecific hydrolysis.

14. A method according to claim 13 in which an (R,S)-2-substituted propionic acid ester is stereospecifically hydrolysed to give the corresponding enantiomeric (S)-acid.

15. A method according to claim 12 wherein the (R,S)-2-substituted propionic acid ester is selected from the group consisting of naproxen, ibuprofen and diclofop ester.

16. A method according to claim 14 wherein the (R,S)-2-substituted propionic ester is selected from the group consisting of naproxen, ibuprofen and diclofop ester.

* * * * *